United States Patent [19]

Kaliner et al.

[11] Patent Number: 4,902,495
[45] Date of Patent: Feb. 20, 1990

[54] IGE FC DIRECTED DELIVERY SYSTEM

[75] Inventors: Michael A. Kaliner, Bethesda; Howard Boltansky, Baltimore, both of Md.

[73] Assignee: The United States of America as represented by the Department of Health and Human Services, Washington, D.C.

[21] Appl. No.: 888,059

[22] Filed: Jul. 22, 1986

[51] Int. Cl.$^4$ .................... A61K 49/02; A61K 39/395
[52] U.S. Cl. ..................................... 424/1.1; 530/387; 530/388; 530/402; 424/9; 424/85.91
[58] Field of Search .............................. 424/1.1, 9, 85; 530/387, 388, 402, 389

[56] References Cited

U.S. PATENT DOCUMENTS

| | | | |
|---|---|---|---|
| 4,331,647 | 5/1982 | Goldenberg | 424/9 X |
| 4,348,376 | 9/1982 | Goldenberg | 424/9 X |
| 4,361,544 | 11/1982 | Goldenberg | 424/9 X |
| 4,624,846 | 11/1986 | Goldenberg | 530/388 X |
| 4,683,292 | 7/1987 | Hahn | 530/328 |

OTHER PUBLICATIONS

Refsnes et al. (1976), J. Exp. Med., 143:1464–1474.
Boltansky et al. (1985), Abstract #320, published in Journal of Allergy and Clinical Immunology, Supplement vol. 75.
Boltansky et al. (1985), Abstract for FASEB Reports, "A Selective Immunotoxin for IgE-Fc Receptor Positive Cells".

Primary Examiner—John S. Maples
Attorney, Agent, or Firm—Mishrilal L. Jain

[57] ABSTRACT

An immunotoxin comprising a conjugate of a toxin with immunoglobulin E or a part thereof and a method delivering the same to a target site is described. Mast cell related abnormalities can be detected by the immunotoxin of the present invention.

7 Claims, 2 Drawing Sheets

IGE FC DIRECTED DELIVERY SYSTEM

BACKGROUND OF THE INVENTION

1. Technical Field

The present invention is related to delivering selected agents through native or cloned IgE or any part thereof capable of binding with specificity to high affinity IgE Fc receptors. More particularly, the present invention is related to a selective delivery system comprising an agent to be delivered being linked in some manner with IgE Fc and targeting such agent to mast cells or basophils which express specific high affinity IgE Fc receptors.

2. State of the Art

The concept of utilizing a specific binding moiety as a vehicle for targeted delivery of a chemotherapeutic agent or toxin is well established. Cancer investigators, for instance, have attempted to exploit monoclonal antibodies to which are linked toxins in the search for selective ablation of tumor cells. The components of such a system are an antibody, a toxic moiety, and an agent for chemically conjugating the antibody with the toxic moiety. Recent reviews summarize the various methods of conjugation and the results of experiments utilizing hybrid molecules, called immunotoxins (*Ghose et al.*, 1983 Academic Press, N.Y. 93:280; *Ghose et al.*, 1978 J. Natl. Cancer Inst. 61:657; *Jansen et al.*, 1980 Immunol. Letters 2:97; *Neville et al.*, 1982 Immun. Review 62:75; *Jansen et al.*, 1982 Immun. Review 62:185).

Although the linking agents utilized for conjugation, the species and isotype of the polyclonal or monoclonal antibodies employed, and the toxins have all been varied, one aspect of the immunotoxin experimentation has generally remained constant in as much as the binding of the immunotoxin to the target cells was accomplished via the Fab' terminus of the antibody portion of the conjugate. The Fc region of an antibody has also been employed as a vehicle for target delivery of a toxin to macrophages (*Refsnes et al.*, 1976 J. Exp. Med. 143:1464). However, the class of antibody employed in such test was IgG.

It should be recognized that there are several known classes of immunoglobulins (Ig), for example IgG, IgM, IgA and IgD. Of course, such classification makes it prima facie evident that each class of immunoglobulin is distinctly different in its structure and function.

A particular class of immunoglobulin, termed IgE, has come to be recognized as being involved in the mechanism responsible for allergic disorders. Like other immunoglobulins, the IgE molecule is comprised of Fab' and Fc portions. The portion designated as Fab' determines the specific material in the body or environment that the molecule will react with, while the Fc portion determines on which cell the molecule will bind.

A variety of cells synthesize and express membrane glycoproteins that can bind the Fc portion of immunoglobulins with variable specificity and affinity. Depending on the degree of specificity and affinity, such Fc receptors can mediate a variety of cellular functions. There are, therefore, at least three factors which determine the functional role of a Fc receptor: (1) the type of Fc involved, that is whether it is an IgG or an IgE Fc and the like; (2) the range of specificity and (3) the degree of binding affinity.

A particular type of Fc receptors is found primarily on mast cells and basophils, which have an extraordinary high affinity for IgE Fc. These receptors are critical for initiating IgE-mediated allergic reactions. The feasibility, role and efficacy of preparing an IgE Fc linked immunotoxin for killing mast cells, basophils or any other cell or tissue which expresses high affinity IgE Fc receptors, have not heretofore been known or determined. It is noted that the mast cell, an effector cell involved in allergic diseases, is widely distributed throughout the body and there is currently a lack of specific therapy for patients with either malignant systemic mastocytosis or severe benign systemic mastocytosis, disorders characterized by an increased proliferation of the mast cells.

SUMMARY OF INVENTION

It is, therefore, an object of the present invention to provide a selective delivery system targeted to high affinity IgE Fc receptors comprising an agent to be delivered having been conjugated with or linked to native or cloned, monomeric or intact IgE Fc or a part thereof.

It is another object of the present invention to provide a method of controlling mast cell or basophil function by a toxic agent, said toxic agent reaching the mast cells or basophils through linkage or conjugation with IgE Fc or any part thereof having high affinity for binding specifically with IgE Fc receptors of mast cells or basophils.

A still further object of the present invention is to provide a means for detecting mast cell tumor and the like by imaging radiolabeled IgE Fc conjugate bound to IgE Fc receptors.

Other objects and advantages of the present invention will become evident as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1:
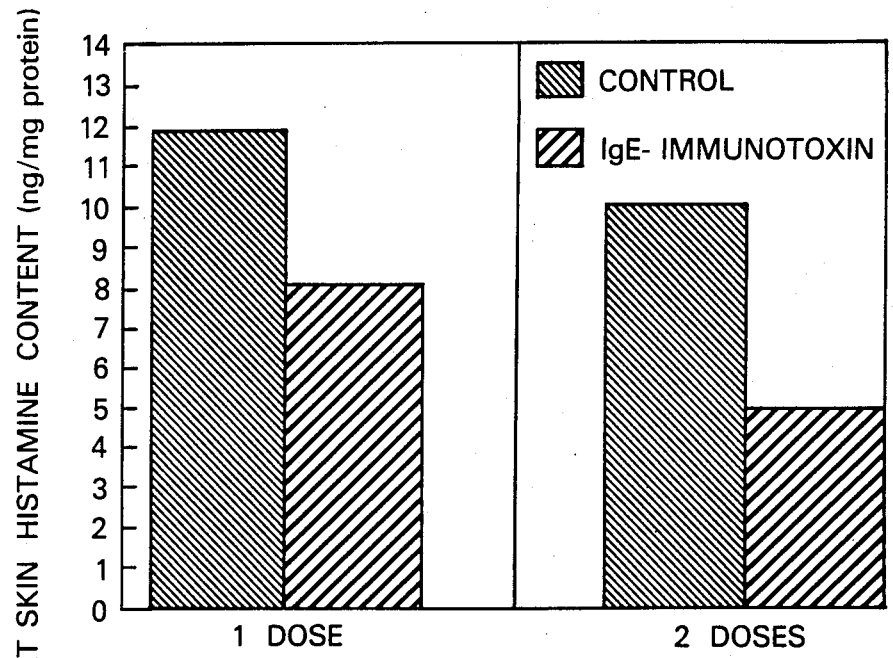
FIG. 1 shows in vivo effect of conjugated and unconjugated IgE-ricin A chain on rat skin histamine content.

The above and other objects and advantages of the present invention are achieved by targeting a selected agent to high affinity IgE Fc receptors using IgE Fc as a specific delivery means therefor.

Unless specifically defined otherwise, all technical or scientific terms used herein have the same meaning as commonly understood by one of ordinary skill in the art to which this invention belongs.

The term "agent" as used herein means any radioactive or non-radioactive entity which binds and/or kills, irreversibly checks or alters the function of specific cell types, such as mast cells, basophils and the like, to which said entity is directed to or targeted against. Examples of such agents are toxins, radioisotopes, drugs, chemicals and the like. Preferred among such agents are intact ricin or isolated A or B chains of ricin, alpha or gamma emitting nuclides such as bismuth-212 or Indium-111 and the like.

The terms "linkage", "linked", "conjugated" and the like as used herein means that the agent has been so made, attached or bonded with respect to IgE or any portion thereof that it is carried to the target in association and concurrently with the binding of said IgE or any portion thereof to high affinity IgE Fc receptors.

The term "high affinity" as used herein means binding affinity, $K_a$ in the range of $10^9$–$10^{10}M^{-1}$ or greater.

Although any methods and materials similar or equivalent to those described herein can be used in the practice or testing of the present invention, the preferred methods and materials are now described. All publications mentioned hereunder are incorporated herein by reference.

MATERIALS AND METHODS

IgE Purification. The rat IgE myeloma protein, IR 162, was purified according to the method of Bazin et al., 1974 J. Immunol. 26:713. Lou/Mn rats (NIH/Small Animal Section, Bethesda, MD) were injected intraperitoneally with minced IR 162 myeloma cells (obtained from Dr. Henry Metzger, NIADDK, NIH Bethesda, MD). At days seven to ten, ascites fluid was harvested and either frozen at $-70°$ C. or passaged to other rats. The frozen ascites fluid was thawed, pooled, filtered through glass wool and dialyzed against 0.2M borate-buffered saline containing 0.15M NaCl, pH 8.0 (BBS). Following 37% ammonium sulfate (Fisher Scientific Co., Silver Spring, MD) precipitation, the precipitate was removed by centrifugation at 10,000 RPM for 30 minutes. The solution was made 48% with respect to ammonium sulfate, centrifuged at about 10,000 RPM for 30 minutes, and the precipitate resuspended in a small volume of 0.025M Tris(Hydroxymethyl) aminomethane-HCl, pH 8.0 (TRIS-HCl). The protein was chromatographed on a 5×30 cm DEAE-Sephadex A-50 (Pharmacia Fine Chemicals, Piscataway, NJ) column equilibrated with TRIS-HCl, pH 8.0. The column was washed with a gradient of 0.05M TRIS-HCl and 0.5M NaCl and the IgE eluted at a conductivity of 9 mS. The protein peak was concentrated by ultramembrane filtration (XM 50 membrane; Amicon Corp. Lexington, MA) and applied to a 2.5×70 cm Sephadex 6B (Pharmacia) column equilibrated with BBS. The proteins eluting in the 180,000 M.W. range were pooled, concentrated by ultramembrane filtration, and stored at $-70°$ C. until used. The protein concentration was determined by the method of Lowry et al., 1951 J. Biol. Chem. 193:265. Sheep anti-rat IgE (Miles Laboratories, Inc. Elkhart, Indiana) formed a single sharp band with this protein in an Ouchterlony immunodiffusion plate.

Ricin. Intact ricin was purified from seeds of *Ricinus communis* according to Nicolson and Blaustein 1972, Biochim. Biophys. Acta. 266:543 as described by Youle and Neville 1979, J. Biol. Chem. 254:11089.

Ricin A Chain. The toxin was purchased from Vector Laboratories, Burlingame, CA. and came supplied at a concentration of 1.0 mg/ml in a buffer of 10 mM HEPES, 0.15M NaCl, 0.08% sodium azide, and 0.01% 2-mercaptoethanol.

Synthesis and Analysis of IgE-Intact Ricin Conjugate. Various methods of preparing conjugated immunotoxins are known in the art and any suitable method could be used, such method per se not being a part of the present invention. The preferred method is now described.

IR 162 IgE (250 μl at 7.5 mg/ml in 0.1M sodium phosphate buffer, pH 8.0) was mixed with 5 μl of 4 mM SPDP (Pharmacia) suspended in ethanol. After one hour at room temperature, 10 μl of 0.625M dithiothreitol in 3M glycine, pH 5.0 was added. The mixture was applied to a 0.75×5 cm Sephadex G-25 (Pharmacia) column equilibrated with 0.05M sodium borate buffer, pH 8.2. The IgE was recovered in a 300 μl volume. To the IgE was added 30 μl (8 mg/ml) of 5,5′ dithiobis(2-nitrobenzoic acid) (Sigma Chemical Co., St. Louis, MO) and the mixture was allowed to react at room temperature for one hour. The mixture was again applied to a 0.75×5 cm Sephadex G-25 column and the protein recovered in a volume of 300 μl with a protein concentration averaging 2.7 mg/ml.

In parallel, intact ricin (1.6 mg at 3.8 mg/ml) was reacted with 50 μl of 4 mM SPDP for one hour in 0.078M sodium borate, pH 8.2. The ricin was desalted by passage over a 1.5×18 cm Sephadex G-25 column equilibrated with phosphate buffered saline (pH 7.5) containing 50 mM lactose. The protein was collected in 1.3 ml with a final concentration of 2.1 mg/ml. One to two 2-pyridyl disulfide groups were usually added to each ricin molecule, as determined by the release of pyridine-2-thione in the presence of 5 mM dithiothreitol.

The entire 2-pyridyl disulfide derivatized ricin fraction and the derivatized IgE fraction were mixed at room temperature. After one hour, the mixture was dialyzed overnight at 4° C. against 0.1M sodium phosphate and 50 mM lactose.

Half of the reaction mixture was applied to a 0.75×60 cm Sephadex TSK 3000 SW (Pharmacia) column in a Hewlett-Packard 1084B HPLC. The column buffer was 0.1M sodium phosphate containing 25 mM lactose, and the flow rate was set to 1 ml/min. Ricin eluted at 21 minutes and IgE at 12.5 minutes. The reaction mixture showed a small shoulder on the IgE peak at 10 min. Material eluting a 9.5 to 15 minutes was collected and pooled. The absorbance at 280 nm of these fractions was 0.652. The conjugate was dialysed against 0.1M sodium phosphate (pH 8.0) and applied to a Sepharose 4B (Pharmacia) column in a Pasteur pipette, equilibrated with 0.1M sodium phosphate (pH 8.0) at 4° C. The column was washed and the IgE-intact ricin eluted with 0.1M lactose. The protein was recovered in 1.2 ml and had an absorbance of 0.9–1.0 at 280 nm. This material is used in all experiments and is referred to as the IgE-intact ricin conjugate.

Synthesis of IgE-Ricin A Chain Conjugate. Since no method has heretofore been developed to allow safe, systemic and efficacious in vivo utilization of immunotoxins containing intact ricin, an alternate approach was also developed. Rat myeloma IgE was, therefore, conjugated via SPDP to the isolated A chain of ricin. Devoid of ricin B chain, this IgE-immunotoxin is preferable for in vivo use as it binds only to cells demonstrating IgE Fc receptors, and is therefore less toxic to non-target cells.

To prepare IgE-ricin A conjugate, IR 162 IgE (1.975 ml of 2 mg/ml) in 0.2M borate-buffered saline containing 0.15M NaCl pH 9.0 (BBS) was reacted with a 20-fold molar excess, $4.4\times10^{-7}$ moles, of SPDP (Sigma Chemical Co., St. Louis, MO) dissolved in 25 μl of ethanol. The mixture was gently turned at room temperature for 45 minutes and then dialyzed against phosphate-buffered isotonic saline pH 7.4 (PBS) at 4° C. overnight. The average number of substituted binding groups per IgE molecule, as determined by a change of absorbance$_{343}$ after reduction, was 9. Ricin A chain (270 μl at 2.0 mg/ml) was reduced in its storage buffer by the addition of 100 mM dithiothreitol for 30 minutes at room temperature. The mixture was chromatographed on a 1.0×27 cm Sephadex G-25 column in PBS at room temperature. The fractions containing ricin A were added immediately to 1.2 ml of 2.0 mg/ml derivatized IgE. The selection of fractions containing ricin A chain was based upon prior determination of the separation of ricin A from residual reducing activity utilizing Ellman's reagent (Ellman, 1959, Arch. Biochem. Biophys. 82:70.). This was important in order to prevent interference with covalent bond formation between the SPDP-derivatized antibody and a native thiol group of ricin A chain by any contaminating dithiothreitol. The IgE-ricin A conjugate was dialyzed against PBS pH 7.4 at 4° C. overnight. The material was then filtered on ultramembranes (XM50 membrane, Amicon Corp., Lexington, MA) and the retentate stored at 4° C. The ratio of ricin A molecules to derivatized IgE molecules in this synthesis averaged 1:1, as assessed by optical density.

SDS-Page. The IgE-ricin A chain conjugate, IR 162, and IgE ricin A chain were analyzed by electrophoresis on 5–15% gradient sodium dodecyl sulfate/polyacrylamide gel electrophoresis (SDS/Page) slab gels (1.5 mm thick) (Ames, 1974, J. Biol. Chem. 249:634). Molecular weight standards were run simultaneously (Bio-Rad Laboratories, Richmond, CA).

All samples were heated to 100° C. for 5 minutes prior to electrophoresis. The reduced samples were heated in the presence of 2% (V/V) 2-mercaptoethanol. The gel was stained with Comassie blue, destained and photographed following standard techniques well known in the art.

Cell-Free Translation Assay. The capacity of ricin A chain to inhibit mRNA translatable protein synthesis was assessed utilizing a cell-free translation assay as described by (Pelham and Jackson, 1976, Eur. J. Biochem, 67:247). All tubes and pipettes were autoclaved prior to use, and all test samples were dialyzed against glass distilled $H_2O$ prior to assay. The reaction mixture contained the following: (1) 7 μl rabbit reticulocyte lysate (Amersham International, Amersham, UK), (2) 2 μci [$^3$H]leucine (58.4 Ci/mmol) (New England Nuclear Corp., Boston, MA), and (3) 400 ng rabbit globin mRNA (Bethesda Research Laboratories, Bethesda, MD). Control samples contained no mRNA. Dilutions of the toxin were added and the reaction mixture cooled to 4° C. and brought to 15 μl final volume with glass distilled water. The mixture was vortexed, centrifuged and incubated (30° C., 1 hr.). Thereafter, 15 μl of 1.0M Tris(Hydroxymethyl)Aminomethane buffer (pH 10.0) was added and the material vortexed, centrifuged, and then incubated at 37° C. for 10 minutes. An aliquot of the reaction mixture (2 μl) was applied to silica gel impregnated glass fiber chromatography sheets (Gelman Inst. Co., Ann Arbor, MI) and air dried. The paper chromatograph was developed in an ascending fashion in 700 μl of a solution containing 6 parts $H_2O$, 3 parts methanol (100%), 1 part glacial acetic acid and 14% trichloracetic acid. The counts which remained within the original spot were cut out and transferred to a fresh vial, air dried overnight, and incubated (60° C., 30 min) in 500 μl Protosol (New England Nuclear Corp.). After cooling, the samples were counted in 10 ml Ultrafluor (National Diagnostics, Somerville, NY).

Percent inhibition of protein translation was determined by the formula:

$$\text{Percent Inhibition} = 100 - \frac{\text{Sample cpm} - \text{background cpm}}{\text{Control cpm} - \text{background cpm}} \times 100$$

Production of Rabbit Anti-IgE and Anti-Ricin A Chain Sera. Rabbits were immunized with 250 μg of either IR 162 IgE or ricin A chain on days 1,14,28,40 and 43. Injection on day 1 was in complete Freund's adjuvant in the foot pads. Injections on day 14 and day 18 were in incomplete Freund's adjuvant, intradermally. All other injections were in PBS intradermally.

The sera were collected, tested for precipitation of the respective protein in a double immunodiffusion plate, and if positive, frozen at −70° C. until used.

Handling of RBL Cells. The 2H3 subline of rats basophilic leukemia (RBL) cells which express high affinity IgE Fc receptors, was maintained in 150 $cm^2$ tissue culture flasks (Costar, Cambridge, MA) in Eagle's minimal essential media with Earle's balanced salt solution supplemented with 4 mM glutamine (M.A. Bioproducts, Walkersville, MD), 40 μg/ml gentamicin sulfate (Schering Corp., Kenilworth, NJ), and 15% heat-inactivated bovine fetal calf serum (Gibco Laboratories, Chagrin Falls, Ohio). The cells were treated with trypsin-versene (M.A. Bioproducts, Walkersville, MD), resuspended in media, and passaged every 3–4 days. Cells were maintained in a 5% $Co_2$ humidified atmosphere at 37° C.

Histamine Release Assay. RBL cells ($10^5$ cell/ml) were aliquoted (1 ml/well) into 24 wells/plate (Costar, Cambridge, MA) and allowed to adhere overnight at 37° C. The media was aspirated and 500 μl fresh media containing 10 μg/ml of the sensitizing protein added. The cells were incubated for one hour at 37° C., the media aspirated and, in experiments assessing the capacity to release histamine immediately after sensitization, the cells were washed twice with 1,4-piperazinediethanesulfonic acid buffer (PIPES-buffer) containing NaCl 119 mM, KCl 5 mM, PIPES 25 mM, glucose 5.6 mM, $Ca^{++}$ 1 mM, $Mg^{++}$ 0.4 mM, and 0.1% bovine serum albumin, pH 7.4. Either rabbit anti-IgE, anti-ricin A chain or nonimmune sera (1:1000) in 500 μl PIPES-buffer was added and the cells incubated for 35 minutes at 37° C. The supernatant and residual histamine were assayed by an automated fluorometric method (Siraganian, 1974, Anal. Biochem. 57:383). Release is expressed as the percentage of histamine released above background as determined by the formula:

$$\text{Percent histamine release above background} = \frac{\text{histamine in supernatant}}{\text{histamine in cells} + \text{histamine in supernatant}} \times 100 - \text{percent background histamine release}$$

For release experiments designed to assess if the conjugate remained bound to the cell surface through 24 hours, the cells were sensitized as described above for one hour, the media aspirated, the cells washed twice and reincubated in 500 μl of fresh media for another 24 hours at which time the media was aspirated, the cells challenged with an antibody in PIPES-buffer and histamine release determined.

Protein Synthesis Assay. The assessment of cytotoxicity in vitro was based on inhibition of [$^3$H]leucine incorporation. Briefly, RBL cells ($5 \times 10^4/100$ μl) were plated in 96 well plates (Costar) and allowed to adhere overnight at 37° C. Varying concentrations of sterile ricin A chain, IgE or IgE-ricin A chain or IgE-intact ricin were added to the media and the incubation continued for one hour at 37° C. The media was aspirated, cells washed with media and then overlayed with media containing varying concentrations of either nonimmune sera, anti-IgE or anti-ricin A chain. The incubation was continued at 37° C. for up to 120 hours at which time [$^3$H]leucine was added and the cells harvested and counted as described below.

In some experiments varying concentrations of monensin (Sigma Chemical Co., St. Louis, MO) or the equivalent amount of ethanol monensin diluent) were present throughout the incubation period following sensitization. In experiments designed to assess if immunologically mediated histamine release was occurring under the test conditions, cells were washed with PIPES-buffer after the initial sensitization and then incubated (37° C., 35 min) in PIPES-buffer containing a 1:100 concentration of either nonimmune sera, anti-IgE or anti-ricin A chain. The buffer was then aspirated and analyzed for histamine (see above), the cells washed and overlayed with media and the incubation continued.

[$^3$H]Leucine (2–3 μCi/well) was added for the final 2–3 hours of incubation. To harvest cells onto filter paper, an automatic cell harvester (Cambridge Technology Inc., Cambridge, MA) was employed. Filters were dried and counted in 2.5 ml Ultrafluor (National Diagnostics).

The results are expressed as percent inhibition of leucine incorporation detected in control cells, and was calculated using the following formula:

$$\text{Percent Inhibition} = 100 - \frac{\text{sample cpm} - \text{background cpm}}{\text{control cpm} - \text{background cpm}} \times 100$$

Each experiment involved triplicate samples and the data represented as the mean+SEM. Statistical analyses were performed employing Student's t-test.

In vivo tests: Describe in vivo protocol including dosage, time course study etc. Only methods, not results).

EXAMPLE 1

The effects of IgE-intact ricin conjugate prepared in accordance with the methods described herein were determined using RBL cells as the test system. The results are shown in Tables 1–6.

TABLE 1

Comparison of the Capacity of IgE and IgE-intact Ricin to Sensitize RBL Cells for Histamine Release

| | Histamine Release (Net Percent) | |
|---|---|---|
| | Buffer | Buffer plus Lactose (50 mm) |
| IgE (ng/ml) | | |
| 1 | 1.0 | 0 |
| 10 | 3.1 | 1.0 |
| 100 | 17 | 10.3 |
| 1000 | ND | 18.6 |
| IgE-intact ricin (ng/ml) | | |

TABLE 1-continued

Comparison of the Capacity of IgE and IgE-intact Ricin to Sensitize RBL Cells for Histamine Release

| | Histamine Release (Net Percent) | |
|---|---|---|
| | Buffer | Buffer plus Lactose (50 mm) |
| 1 | 1.0 | 2.2 |
| 10 | 6.5 | 3.8 |
| 100 | 16.7 | 12.8 |
| 1000 | ND | 23 |

RBL cells were sensitized with IgE or IgE-intact ricin for 30 minutes at 37° C., washed twice with PIPES-buffer and anti-rat IgE (1:1000) in PIPES-buffer was added for 35 minutes. The PIPES-buffer employed contained 50 mM lactose in a portion of the experiments. Controls were incubated in parallel but challenged with PIPES-buffer or PIPES-buffer plus lactose in the absence of anti-IgE. Background histamine release was between 5 and 7 percent in all experiments. The net percent histamine release values represent the average of two separate experiments performed in duplicate. ND = not determined.

TABLE 2

Capacity of Lactose to Prevent Ricin Cytotoxicity

| | [$^3$H]Leucine Incorporation (cpm − mean ± SEM) |
|---|---|
| Exp. 1. | |
| Control | 19872 ± 1256 |
| Ricin (20 ng/ml) | 3998 ± 351 |
| Control + Lactose (50 mM) | 18779 ± 330 |
| Ricin (20 ng/ml) + Lactose (50 mM) | 19340 ± 2035 |
| Ricin (12 ng/ml) | 8875 ± 265 |
| Ricin (12 ng/ml) + Lactose (50 mM) | 18267 ± 1048 |
| Exp. 2 | |
| Control | 37634 ± 478 |
| Ricin (10 ng/ml) | 9454 ± 402 |
| Control + Lactose (50 mM) | 29663 ± 1042 |
| Ricin (10 ng/ml) + Lactose (50 mM) | 31560 ± 872 |

RBL cells were incubated with varying concentrations of intact ricin in media alone or media containing 50 mM lactose for 2 hours. Controls were incubated in parallel in media alone or media containing 50 mM lactose. [$^3$H]Leucine (1–2 μCi/well) was then added for 2 hours and the cells harvested and counted as described in the text. Results represent average ± SEM cpm of triplicate samples from 2 separate experiments.

TABLE 3

Effect of Lactose on IgE-intact Ricin Cytotoxicity

| | Percent [$^3$H] Leucine Incorporation Compared to Control |
|---|---|
| Control | 100 |
| IgE-intact ricin (60 ng/ml) | 19 |
| Control + Lactose (50 mM) | 93 |
| IgE-intact ricin (60 ng/ml) + Lactose (50 mM) | 72 |

RBL cells were incubated with IgE-intact ricin (60 ng/ml) in media alone or media containing 50 mM lactose for 2 hours. controls were incubated in parallel in media alone or media containing 50 mM lactose. [$^3$H] Leucine (1–2 μCi/well) was then added for 2 hours and the cells harvested and counted as described in the text. Control cells in buffer alone incorporated 38002 ± 492 cpm. Results represent average percent [$^3$H] leucine incorporation of triplicate samples.

TABLE 4

The Capacity of Lactose to Interfere with IgE-intact Ricin Cytotoxicity

| | IgE-intact ricin (ng/ml) | [$^3$H]Leucine Incorporation (cpm − mean ± SEM) Media | Media plus Lactose (50 mM) |
|---|---|---|---|
| Exp. A | 300 | 86 ± 14 | 99 ± 18 |
| | 150 | 71 ± 17 | 190 ± 38 |
| | 100 | 66 ± 4 | 909 ± 216 |
| | 30 | 66 ± 6 | 2336 ± 172 |
| | Control | 3555 ± 686 | 2862 ± 243 |
| Exp. B | 30 | 380 ± 8 | 4795 ± 118 |
| | 10 | 1327 ± 418 | 4012 ± 860 |

TABLE 4-continued The Capacity of Lactose to Interfere with IgE-intact Ricin Cytotoxicity

| IgE-intact ricin (ng/ml) | [$^3$H]Leucine Incorporation (cpm − mean ± SEM) Media | Media plus Lactose (50 mM) |
|---|---|---|
| 5 | 3771 ± 406 | 5456 ± 1631 |
| 1 | 4895 ± 800 | 4268 ± 92 |
| Control | 6502 ± 106 | 5410 ± 1287 |

Two separate experiments (A and B) in which RBL cells were incubated with IgE-intact ricin at varying doses for 24 hours are presented. The results represent the incorporation of [$^3$H]leucine into protein and are the mean ± SEM of triplicates. The media column indicates results of cells exposed to IgE-intact ricin in media while the lactose column indicates the incorporation of 50 mM lactose into the media system. Control wells were carried in parallel and had no proteinadded.

TABLE 5

The Effect of IgE Preincubation on IgE-intact Ricin Cytotoxicity

| | Experimental Condition | Leucine Incorporation (cpm − mean ± SEM) No IgE preincubation | IgE preincubation |
|---|---|---|---|
| EXP. A | With Lactose: | | |
| | IgE-intact ricin (100 ng/ml) | 1479 ± 111 | 2775 ± 245 |
| | Control | 3593 ± 304 | 3470 ± 350 |
| | Without Lactose: | | |
| | IgE-intact ricin (100 ng/ml) | 432 ± 81 | 323 ± 14 |
| | Control | 2586 ± 112 | 2627 ± 318 |
| EXP. B | With Lactose: | | |
| | IgE-intact ricin (60 ng/ml) | 27158 ± 248 | 31824 ± 420 |
| | Control | 37634 ± 478 | 30298 ± 299 |
| | Without Lactose: | | |
| | IgE-intact ricin (60 ng/ml) | 7134 ± 1522 | 6228 ± 185 |
| | Control | 32635 ± 1667 | 35632 ± 2578 |

RBL cells were incubated for one hour with or without free IgE (1 μg/ml). IgE-intact ricin (60 or 100 ng/ml) was then added to cells in media alone or media containing 50 mM lactose. The cells were incubated for 24 hours at which time [$^3$H]leucine (1–2 μCi/well) was added for a 2 hour incubation. The cells were harvested and counted as described in the text. Control wells were carried in parallel. Results represent average ± SEM cpm of triplicate samples.

TABLE 6

Summary of Experiments Demonstrating Residual IgE-intact Ricin Cytotoxicity in the Presence of Lactose.

| Experiment | Cytotoxicity Percent Reduction of [$^3$H]leucine Incorporation Compared to Controls: Media | Media Plus Lactose (50 mM) |
|---|---|---|
| (1) 2 hour incubation, IgE-intact ricin, | | |
| 60 ng/ml | 81 | 15 |
| (2) 18 hour incubation, IgE-intact ricin, | | |
| 30 ng/ml | 73 | 22 |
| (3) 24 hour incubation, IgE-intact ricin, | | |
| 30 ng/ml | 95 | 34 |
| (4) 24 hour incubation, IgE-intact ricin, | | |
| 100 ng/ml | 98 | 32 |
| 50 ng/ml | 97 | 34 |
| 30 ng/ml | 98 | 18 |
| (5) 24 hour incubation, IgE-intact ricin, | | |
| 30 ng/ml | 99 | 24 |
| 10 ng/ml | 99 | 31 |
| 5 ng/ml | 98 | ND |
| 1 ng/ml | 87 | 17 |
| (6) 24 hour incubation, IgE-intact ricin, | | |
| 30 ng/ml | 96 | 11 |
| 10 ng/ml | 80 | 26 |
| 1 ng/ml | 25 | 21 |
| (7) 24 hour incubation, IgE-intact ricin, | | |
| 100 ng/ml, and anti-IgE (1:1000) | 87 | 74 |

RBL cells were incubated with varying doses of IgE-intact ricin for 2–24 hours in either media alone or media containing 50 mM lactose. After the defined time of incubation [$^3$H]leucine (1–2 μCi/well) was added and the incubation continued for 2 hours. The cells were harvested and counted as described in the text. In experiment number 7, after one hour incubation with the IgE-immunotoxin, the cells were washed and anti-IgE (1:1000) in PIPES-buffer was added for 35 minutes at 37° C. The cells were then washed and the incubation in media continued for 24 hours. Results reflect an average percent reduction of [$^3$H]leucine incorporation of triplicate samples. Controls were carried in parallel.
ND = not determined.

The data presented in Tables 1–6 clearly demonstrate that IgE-immunotoxin is comparable to free IgE in its ability to sensitize and non-cytotoxically release histamine from rat basophilic leukemia cells (IgE Fc receptor positive) after anti-IgE exposure (Table 1).

Lactose competitively inhibits binding of ricin to galactose-containing glycoproteins on cell surfaces (Table 2). Ricin and the IgE-intact ricin conjugate demonstrated dose-related cytotoxicy towards rat basophilic leukemia cells in the absence of lactose (Tables 2–4). Cytotoxicity of free ricin could be inhibited by lactose below a certain concentration of the free toxin. Lactose, however, was not fully able to inhibit the cytotoxicity of the IgE-intact ricin. The residual, lactose-non-inhibitable, toxicity was attributed to IgE Fc mediated binding (Table 5) and internalization of the immunotoxin as this cytotoxicity could be partially inhibited by preincubation with free IgE (Tables 5–6).

EXAMPLE 2

The effects of IgE-ricin A chain conjugate prepared in accordance with the method described herein were determined using RBL cells as the test system.

In order to ascertain the formation of a conjugate via heterobifunctional SPDP linkage between the purified IgE and freshly reduced ricin A chain, the conjugate (which was dialyzed and filtered on ultramembranes to remove unbound entities) was electrophoresed on 5–15% SDS-Page. The results (not shown) confirmed the formation of an IgE-ricin A chain conjugate (hereinafter IgE-ricin A).

Tables 7–12 show the effect of IgE-ricin A on the model RBL cell system. Tables 7–8 demonstrate histamine release from rat basophilic leukemia cells after sensitization with IgE-ricin A chain and aggregation with either anti-IgE or anti-ricin A chain, indicating that the conjugate retained antibody binding activity. The immunotoxin was toxic in a cell-free translation assay indicating retention of ricin A chain ribosomal inactivating activity (Tables 9–11). In the presence of the carboxylic ionophore, monensin, the conjugate could kill rat basophilic leukemia cells via IgE Fc receptor binding (Table 12). The cytotoxicity was significantly inhibited by aggregation of the IgE-ricin A chain with anti-IgE and totally inhibited by aggregation with anti-ricin A chain. These results clearly establish that IgE-ricin A chain conjugate kills RBL cells via IgE Fc receptor binding and internalization, in vitro.

TABLE 7

Comparison of the Ability of IgE-ricin A Chain Versus Free IgE, Free Ricin A chain or Free IgE Plus Free Ricin A Chain to Sensitize RBL Cells for Histamine Release

| Sensitizing Protein (5 μg/$10^5$ RBL cells) | Immune Sera | Percent Histamine Release Above Background |
|---|---|---|
| None | nonimmune | 0 |
|  | anti-IgE | 0 |
|  | anti-ricin A chain | 0 |
| Ricin A chain | nonimmune | 0 |
|  | anti-IgE | 0 |
|  | anti-ricin A chain | 0 |
| IgE | nonimmune | 5 |
|  | anti-IgE | 28 |
|  | anti-ricin A chain | 5 |
| IgE plus ricin A chain | nonimmune | 4 |
|  | anti-IgE | 30 |
|  | anti-ricin A chain | 4 |
| IgE-ricin A chain conjugate | nonimmune | 3 |
|  | anti-IgE | 34 |
|  | anti-ricin A chain | 31 |

RBL cells were incubated for one hour at 37° C. in the presence of the sensitizing protein(s). Cells were then washed with PIPES-buffer and incubated for 35 minutes in 1:1000 final concentration of the immune sera in PIPES-buffer. The supernatant was removed and analyzed for histamine content. Percent histamine release was determined by analyzing the residual histamine within the cells and dividing the amount released by the sum of the amount released and the residual cellular histamine and multiplying this number by 100. Percent histamine release above background reflects the average of wells tested in duplicate minus the background percent release. In this experiment background release was 11%.

TABLE 8

Comparison of the Ability of IgE-ricin A Chain or IgE to Sensitize RBL Cells and Release Histamine After 24 Hours Incubation

| Sensitizing Protein (5 μg/$10^5$ RBL cells) | Immune Sera | Percent Histamine Release Above Background |
|---|---|---|
| None | nonimmune | 0 |
|  | anti-IgE | 0 |
|  | anti-ricin A chain | 0 |
| IgE | nonimmune | 0 |
|  | anti-IgE | 13 |
|  | anti-ricin A chain | 0 |
| IgE-ricin A chain conjugate | nonimmune | 0 |
|  | anti-IgE | 13 |
|  | anti-ricin A chain | 14.5 |

RBL cells were incubated for one hour at 37° C. in the presence of the sensitizing protein. Cells were then washed twice with media and incubated for an additional 24 hours in media. Cells were then washed with PIPES-buffer and incubated for 35 minutes in a 1:1000 final concentration of the immune sera diluted in PIPES-buffer. Background release was 8% in this experiment.

TABLE 9

Measurement of IgE-ricin A Chain Cytotoxicity After Aggregation with Varying Concentrations of Anti-IgE or Anti-ricin A Chain

| Sensitizing Protein (10 μg/ml) | Immune Sera |  | [$^3$H] leucine Incorporation (cpm ± SEM) |
|---|---|---|---|
| None | nonimmune | 1:10 | 29031 ± 1857 |
|  |  | 1:100 | 24151 ± 442 |
|  |  | 1:500 | 27712 ± 2749 |
|  |  | 1:10,000 | ND |
|  | anti-IgE | 1:10 | 28076 ± 1194 |
|  |  | 1:100 | 34513 ± 4178 |
|  |  | 1:500 | 35141 ± 2252 |
|  |  | 1:10,000 | ND |
|  | anti-ricin A chain | 1:10 | 32445 ± 2822 |
|  |  | 1:100 | 30907 ± 4556 |
|  |  | 1:500 | 37759 ± 1621 |
|  |  | 1:10,000 | ND |
| IgE | nonimmune | 1:10 | 31714 ± 3179 |
|  |  | 1:100 | 34520 ± 2813 |
|  |  | 1:500 | 33859 ± 1435 |
|  |  | 1:10,000 | 35556 ± 1867 |
|  | anti-IgE | 1:10 | 24773 ± 2271 |
|  |  | 1:100 | 32342 ± 242 |
|  |  | 1:500 | 38176 ± 893 |
|  |  | 1:10,000 | 37263 ± 2780 |
|  | anti-ricin A chain | 1:10 | 34154 ± 2001 |
|  |  | 1:100 | 23744 ± 1980 |
|  |  | 1:500 | 36350 ± 2586 |
|  |  | 1:10,000 | 37050 ± 3592 |
| Ricin A Chain | nonimmune | 1:10 | 44310 ± 3310 |
|  |  | 1:100 | 44403 ± 1575 |
|  |  | 1:500 | 46005 ± 2337 |
|  |  | 1:10,000 | ND |
|  | anti-IgE | 1:10 | 26907 ± 936 |
|  |  | 1:100 | 39185 ± 843 |
|  |  | 1:500 | 40655 ± 1642 |
|  |  | 1:10,000 | ND |
|  | anti-ricin A chain | 1:10 | 32638 ± 876 |
|  |  | 1:100 | 37315 ± 558 |
|  |  | 1:500 | 33775 ± 3668 |
|  |  | 1:10,000 | ND |
| IgE-ricin A chain conjugate | nonimmune | 1:10 | 36122 ± 9756 |
|  |  | 1:100 | 34645 ± 794 |
|  |  | 1:500 | 34820 ± 2569 |
|  |  | 1:10,000 | 30678 ± 1879 |
|  | anti-IgE | 1:10 | 20262 ± 1004 |
|  |  | 1:100 | 32603 ± 959 |
|  |  | 1:500 | 34752 ± 1244 |
|  |  | 1:10,000 | 29882 ± 798 |
|  | anti-ricin A chain | 1:10 | 29569 ± 5054 |
|  |  | 1:100 | 34390 ± 2677 |
|  |  | 1:500 | 34274 ± 914 |
|  |  | 1:10,000 | 22973 ± 1207 |

RBL cells were incubated for one hour at 37° C. in the presence of the test protein (10 μg/ml). The cells were then washed and overlayed with 100 μl of media containing varying concentrations of nonimmune sera, anti-IgE or anti-ricin A chain. The incubation was continued for 96 hours and the cells harvested and counted as described. Results are expressed as the average cpm ± SEM of triplicate samples.
ND = not determined

TABLE 10

Measurement of IgE-ricin A Chain Cytotoxicity Employing a Higher Dose

| Sensitizing Protein (120 μg/ml) | Immune Sera (1:100) | [$^3$H] leucine Incorporation (cpm ± SEM) |
|---|---|---|
| None | nonimmune | 6714 ± 1272 |
|  | anti-IgE | 7640 ± 629 |
|  | anti-ricin A chain | 7258 ± 30 |
| IgE | nonimmune | 5983 ± 106 |
|  | anti-IgE | 5883 ± 224 |
|  | anti-ricin A chain | 6070 ± 379 |
| Ricin A chain | nonimmune | 6302 ± 371 |
|  | anti-IgE | 5726 ± 212 |
|  | anti-ricin A chain | 6343 ± 450 |
| IgE-ricin A chain conjugate | nonimmune | 4513 ± 739 |
|  | anti-IgE | 4462 ± 111 |
|  | anti-ricin A chain | 4284 ± 608 |

RBL cells were incubated for one hour at 37° C. in the presence of the sensitizing protein. Cells were then washed and incubated for 35 minutes at 37° C. in PIPES-buffer containing 1:100 final concentration of nonimmune sera, anti-IgE or anti-ricin A chain. The buffer was removed, histamine release determined, and the cells then incubated in media for 96 hours. Results are expressed as the average cpm ± SEM of triplicate samples.

TABLE 11

Time-course of IgE-ricin A Chain Cytotoxicity

| Immune Sera (1:50) | Incubation Time (hours) | Sensitizing Protein (60 μg/ml) | | | |
|---|---|---|---|---|---|
| | | None | IgE | Ricin A Chain | IgE-ricin A Chain Conjugate |
| | | [³H]leucine Incorporation (cpm ± SEM) | | | |
| nonimmune | 24 | 5586 ± 1333 | 3190 ± 462 | 3633 ± 735 | 2413 ± 222 |
| | 72 | 2871 ± 390 | 3283 ± 378 | 3839 ± 691 | 3673 ± 212 |
| | 120 | 2875 ± 163 | 2741 ± 208 | 3174 ± 346 | 2538 ± 375 |
| anti-IgE | 24 | 4415 ± 347 | 3487 ± 106 | 2960 ± 138 | 2981 ± 550 |
| | 72 | 4046 ± 235 | 3561 ± 528 | 3681 ± 139 | 4326 ± 265 |
| | 120 | 3012 ± 208 | 2834 ± 280 | 2858 ± 208 | 2571 + 228 |
| anti-ricin A chain | 24 | 3777 ± 315 | 4684 ± 887 | 3636 ± 203 | 2988 ± 112 |
| | 72 | 3416 ± 482 | 6615 ± 1689 | 3625 ± 507 | 4733 ± 509 |
| | 120 | 3462 ± 262 | 2398 ± 218 | 2791 ± 343 | 2340 ± 246 |

RBL cells were sensitized for one hour at 37° C., washed and then overlayed with media containing either nonimmune sera, anti-IgE or anti-ricin A chain at a 1:50 final concentration. Cells were then incubated for the specified time, pulsed and counted as described. Results are expressed as the average cpm ± SEM of triplicate samples.

TABLE 12

Effect of Monensin on IgE-ricin A Chain Toxicity

| | Incubation Time (hours) | Sensitizing Protein (60 μg/ml) | [³H]leucine Incorporation (cpm ± SEM) | |
|---|---|---|---|---|
| | | | Ethanol | Monensin ($10^{-7}$ M) |
| Experiment A | 40 | IgE | 15366 ± 2040 | 10635 ± 498 |
| | | IgE-ricin A chain | 12325 ± 171 | 2602 ± 1447 |
| Experiment B | 48 | IgE | 16825 ± 564 | 5214 ± 553 |
| | | IgE-ricin A chain | 15916 ± 1142 | 0 |
| Experiment C | 65 | IgE | 9418 ± 819 | 4275 ± 74 |
| | | IgE-ricin A chain | 10655 ± 539 | 922 ± 932 |

RBL cells were sensitized for one hour at 37° C., washed and then incubated in media containing monensin ($10^{-7}$ M) or the equivalent concentration of ethanol for 40-65 hours. Cells were then pulsed with [³H]leucine and harvested as described. Data is presented as the average cpm ± SEM of triplicate samples.

EXAMPLE 3

The in vivo efficacy of IgE-ricin A conjugate was tested in a rat model system. FIG. 1 shows a comparison of the effects of injecting 1 or 2 doses of 10 μg of the preparation on the skin histamine content. The data indicate that the skin histamine content is reduced by more than 50% by the use of 2 injections of the conjugate while the use of a single injection reduces the histamine content but not by the same degree. Skin histamine content can be substantially reduced with one injection of IgE-ricin a chain but this effect requires larger quantities of IgE-toxin.

The appropriate control for histamine depletion is the effect of anti-IgE which induces skin mast cell degranulation. What is found after anti-IgE administration is a reduction of skin histamine which lasts several hours and is fully repleted in 4-6 hours. Thus, the depletion of skin histamine noted herein cannot be attributed to simply causing mast cells to degranulate.

Figure 2:
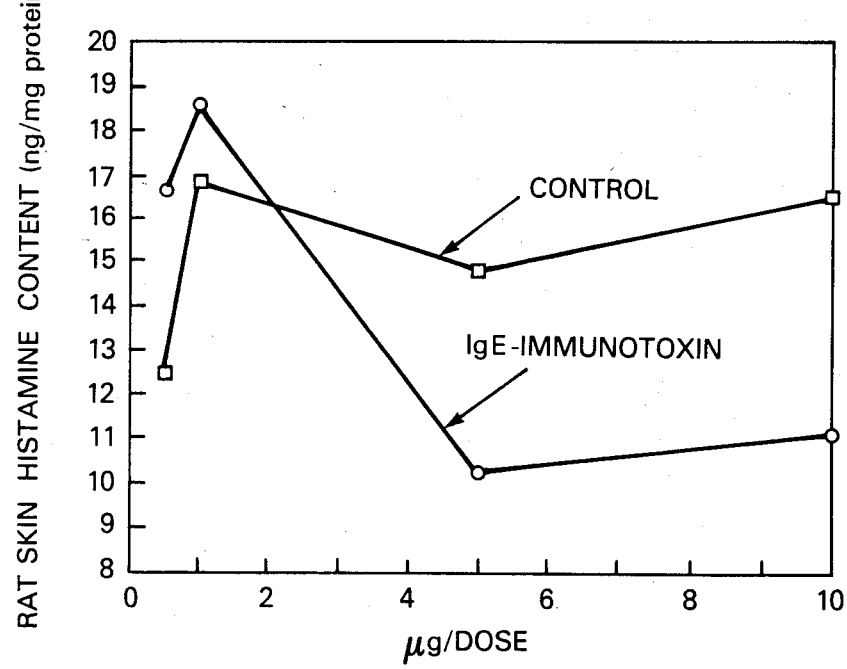
FIG. 2 shows dose-response curves of in vivo treatment of conjugated IgE-ricin A.
Figure 3:
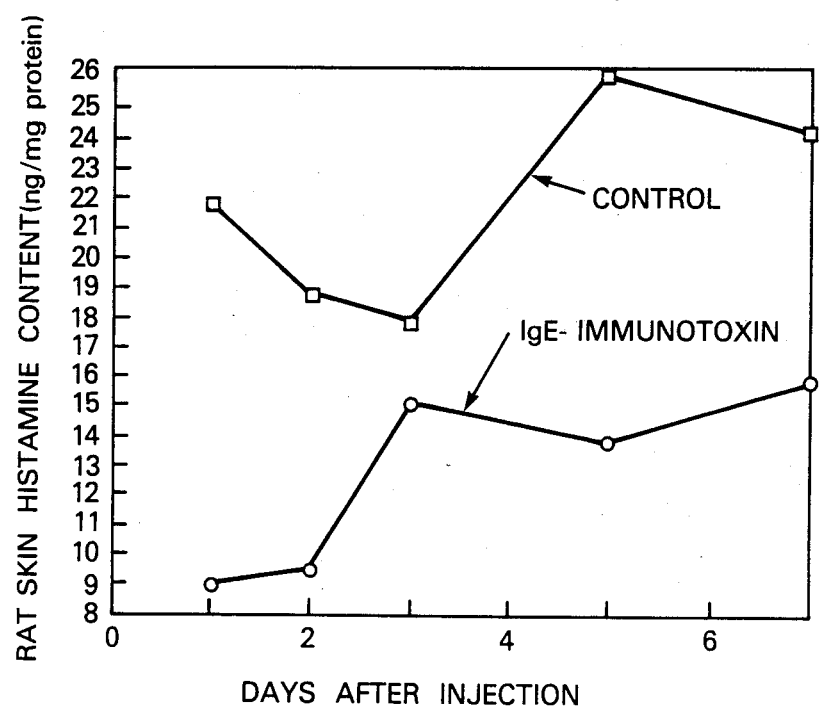
FIG. 3 shows time course of in vivo response to conjugated and unconjugated IgE-ricin A.

FIG. 2 shows a dose-response of 2 doses of IgE-toxin compared to the unconjugated combination of IgE and ricin A, designated IgE plus ricin. Doses of 5 and 10 but not 0.5 or 1 μg of the conjugate were effective. FIG. 3 shows the time course of skin histamine depletion after 2 injections of IgE-toxin compared to IgE plus toxin. Skin histamine is maximally reduced 24-48 hours after the second dose of IgE-toxin administration, and the depletion persists through at least 7 days.

These data clearly show that the IgE toxin can deplete skin of histamine and that this effect persists through several days. This evidence confirms the in vitro data and extends it to show that the delivery system works in vivo as well. Of course, mast cells being the major source of tissue histamine the effect of IgE-toxin on these cells is remarkably noteworthy.

EXAMPLE 4

Bismuth-212 is produced by a modification of a published mehtod (Zucchini and Friedman, 1982, Int. J. Nucl. Med. Biol. 9:83). The modification is detailed in the publication of Kozak, et al., 1986 Proc. Nat. Acad. Sciences 83:474 and is as follows: The generator is eluted with 0.75 ml HCl 2M to produce Pb-212-Bi which is evaporated to dryness by vacuum centrifugation (Savant Instruments), redissolved in 250 μl 0.1M HCl and Pb-212 quantitatively absorbed on a 1×2.5 mm column of Ag-50WX4 (200-400 mesh) H+ form resin (Bio-Rad) and rinsed with 2 ml deionized water. After 2 hr, Bi-212 is eluted with 0.15 ml 0.1M HI.

For protein incorporation, the Bi-212-HI solution (about 3 mCi) is reduced to 50 μl volume and brought to pH 4-4.5 with a 0.3M phosphate, 0.10M acetate solution, pH 6.9 and immediately reacted for 15 min. with IgE. The resulting Bi-212-labeled IgE is purified by high performance liquid chromtography on a TSK-3000 column, 0.1M PBS eluant.

The Bismuth-212 is conjugated to the IgE molecule or IgE Fc fragment through a linkage employing diethylenetriaminepentaacetic acid (DTPA). A modification of the method of Krejcarek and Tucker, 1977, Biochem. Biophys. Res. Comm. 77:581 is used to link DTPA to IgE with C-14-DTPA employed to quantify chelate-to-antibody ratio. DTPA (0.2 mM) is dissolved in 2 ml H₂O by addition to triethylamine (1.38 mM) and lyophilized. The solid form is taken up in 1.0 ml of acetonitrile at 4 degrees celsius and treated with isobutylchloroformate (0.27 mM) for 30 min., centrifuged, and a 20 μl aliquot of isobutylcarboxycarbonic anhydride solution is reacted at 4 degrees celsius for 1.5 hr. with IgE in 50 mM $NaHCO_3$, pH 8.0. Sequential dialyses in metal free buffer are employed to purify protein. The first dialysis solution is 50 mM citrate pH 5.5, 0.15M NaCl, 0.0001M ascorbic acid, and the final dialysis solution is 0.1M PBS pH 7.4. About 2 ml chelex ion exchange resin (Bio-Rad) is added to all citrate dialysis solutions.

For labeling with Bi-212, DTPA-IgE is dialyzed 2–4 hr. into 20 mM MES pH 6.0 (2-(N-morpholino)-ethanesulfonic acid) sodium salt, (Calbiochem-Behring, La Jolla, CA) just prior to use. The IgE-Bismuth 212, by virtue of the selected delivery of an alpha-emitting nuclide, is able to selectively kill cells possessing IgE Fc receptors. In vitro cytotoxicity is assayed by 3H-leucine incorporation and limiting dilution assays. The properties of Bismuth-212 which make it valuable for radioimmunotherapy include its short half-life, relatively small radius of energy deposition and the availability of the reagent from a radium generator. The advantage of an alpha emitter as the toxic moiety of an IgE-conjugate is that only one or two particles need hit a cell nucleus to cause death and the antibody (IgE) need only deliver the isotope to the surface of the cell for effectiveness, thus avoiding the necessity and possible problems inherent with toxic agents requiring internalization.

EXAMPLE 5

Indium-111 (New England Nuclear Corp.) is conjugated to rat IgE via DTPA as outlined in Example 4. This isotope is able to bind to rat basophilic leukemia cells (RBL cells) in vitro and is also shown to persist on RBL cells labeled in vitro and then grown as a subcutaneous tumor in rats. The isotope labeled IE is demonstrated on the RBL cells by both quantitative gamma counting of harvested tissue and by whole body gamma camera scintigraphs (data not shown). Human IgE or IgE Fc fragments, DTPA derivatized by the above procedure, are synthesized and Indium-111 bound to the antibody protein through the conjugating agent.

Tissue bound IgE-Indium 111 conjugates are visualized by the non-invasive method of whole body gamma camera scanning. Thus, IgE-Indium 111 provides a valuable and safe isotope for demonstrating mast cells by localization of the IgE-bound isotope. Hence, patients with excess mast cells (either mastocytosis or mastocytomas) through an injection of the IgE-Indium 111 and a whole body gamma camera scan, can be screened for mast cell distribution and density. Such techniques provide an excellent diagnostic test for disease in which mast cell number is increased.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An immunotoxin comprising a conjugate of a toxin with immunoglobulin E (IgE) or a part thereof, said conjugate being capable of binding specifically with IgE Fc receptors with an affinity of equal or greater than $10^9M^{-1}$, said conjugate being suitable for use in vivo, wherein said toxin is bismuth$^{212}$ or indium$^{111}$.

2. The immunotoxin of claim 1 wherein said toxin is bismuth$^{212}$.

3. The immunotoxin of claim 1 wherein said toxin is Indium$^{111}$.

4. The immunotoxin of claim 1 wherein said receptors are mast cell or basophil receptors.

5. A method of delivering a toxic agent to a target cell or tissue located in a host, wherein said cell or tissue expressing IgE Fc receptors of equal or greater than $10^9M^{-1}$ binding affinity comprising conjugating a toxic agent with monomeric or intact immunoglobulin E or a portion thereof, wherein said conjugate possesses an Fc fraction and administering an effective amount of said conjugate to said host.

6. The method of claim 5 wherein said cells are mast cells or basophils.

7. A method of detecting mast cell tumors, benign mastocytosis or mast cell number comprising systemically delivering an effective amount of a conjugate of IgE Fc and a radiolabeled agent to a host suspected of having a mast cell tumor, benign mastocytosis or disease process involving mast cells, and obtaining a radiographic image of said host or of a body part thereof.

* * * * *